(12) United States Patent
Mudd et al.

(10) Patent No.: US 8,992,481 B2
(45) Date of Patent: *Mar. 31, 2015

(54) MODULAR INJECTION DEVICE
(71) Applicant: Allergan, Inc., Irvine, CA (US)
(72) Inventors: Christopher Mudd, Ventura, CA (US); Ahmet Tezel, Santa Barbara, CA (US); Shaohui Qiu, Belmont, MA (US); Lee Powers, Somerville, MA (US)
(73) Assignee: Allergan, Inc., Irvine, CA (US)
( * ) Notice: Subject to any disclaimer, the term of this patent is extended or adjusted under 35 U.S.C. 154(b) by 30 days.

This patent is subject to a terminal disclaimer.

(21) Appl. No.: 13/915,194
(22) Filed: Jun. 11, 2013
(65) Prior Publication Data
US 2013/0274670 A1   Oct. 17, 2013

Related U.S. Application Data
(63) Continuation of application No. 13/111,731, filed on May 19, 2011, now Pat. No. 8,480,630.
(60) Provisional application No. 61/346,354, filed on May 19, 2010.

(51) Int. Cl.
*A61M 5/32* (2006.01)
*A61M 5/20* (2006.01)
(Continued)

(52) U.S. Cl.
CPC ............. *A61M 5/20* (2013.01); *A61M 5/14244* (2013.01); *A61M 5/14546* (2013.01); *A61M 5/1413* (2013.01); *A61M 5/14566* (2013.01); *A61M 5/3129* (2013.01); *A61M 2005/2407* (2013.01); *A61M 2005/2496* (2013.01);
(Continued)

(58) Field of Classification Search
CPC . A61M 5/14566; A61M 5/20; A61M 5/1413; A61M 2205/586
USPC .......................................... 604/131–155, 179
See application file for complete search history.

(56) References Cited

U.S. PATENT DOCUMENTS 2,737,946 A   3/1956   Hein, Jr.
2,853,070 A   9/1958   Maurice
(Continued)

FOREIGN PATENT DOCUMENTS

EP   0362484   4/1990
EP   1051988   11/2000
(Continued)

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968, XP055055114.
(Continued)

*Primary Examiner* — Nicholas Lucchesi
*Assistant Examiner* — Gerald Landry, II
(74) *Attorney, Agent, or Firm* — Linda Allyson Nassif

(57) ABSTRACT

A modular injection device for administration of dermal filler compositions is provided. The injection device may include a handheld injector unit including a drive unit, the drive unit configured to apply an extrusion force to a fluid; a control unit remote from the injector unit, the control unit configured to control the drive unit; and a cable configured to connect the control unit to the injector unit.

16 Claims, 15 Drawing Sheets

(51) Int. Cl.
*A61M 5/142* (2006.01)
*A61M 5/145* (2006.01)
*A61M 5/14* (2006.01)
*A61M 5/31* (2006.01)
*A61M 5/24* (2006.01)

(52) U.S. Cl.
CPC .............. *A61M 2005/3125* (2013.01); *A61M 2005/3126* (2013.01); *A61M 2205/14* (2013.01); *A61M 2205/3334* (2013.01); *A61M 2205/586* (2013.01); *A61M 2205/8206* (2013.01); *A61M 2205/8268* (2013.01); *A61M 2209/086* (2013.01); *A61M 2209/088* (2013.01)
USPC ........................................ 604/179; 604/154

(56) References Cited

U.S. PATENT DOCUMENTS

| | | | |
|---|---|---|---|
| D202,754 S | 11/1965 | Naftolin | |
| D214,112 S | 5/1969 | Langdon | |
| D224,066 S | 6/1972 | McDonald | |
| 3,720,211 A * | 3/1973 | Kyrias | 604/155 |
| 3,807,048 A | 4/1974 | Malmin | |
| 4,240,423 A | 12/1980 | Akhavi | |
| 4,240,426 A | 12/1980 | Akhavi | |
| 4,273,122 A | 6/1981 | Whitney et al. | |
| 4,326,517 A | 4/1982 | Whitney et al. | |
| 4,529,401 A | 7/1985 | Leslie et al. | |
| 4,699,612 A | 10/1987 | Hamacher | |
| D303,010 S | 8/1989 | Jabbusch | |
| 4,869,717 A | 9/1989 | Adair | |
| 5,024,656 A | 6/1991 | Gasaway et al. | |
| 5,046,506 A | 9/1991 | Singer | |
| 5,100,390 A | 3/1992 | Lubeck et al. | |
| 5,104,375 A | 4/1992 | Wolf et al. | |
| 5,127,436 A | 7/1992 | Campion et al. | |
| 5,141,496 A | 8/1992 | Dalto et al. | |
| 5,295,980 A | 3/1994 | Ersek | |
| 5,305,788 A | 4/1994 | Mayeux | |
| 5,322,511 A | 6/1994 | Armbruster et al. | |
| 5,344,407 A | 9/1994 | Ryan | |
| 5,383,851 A | 1/1995 | Mackinnon, Jr. et al. | |
| 5,405,330 A | 4/1995 | Zunitch et al. | |
| D378,939 S | 4/1997 | Smith et al. | |
| 5,690,618 A | 11/1997 | Smith et al. | |
| 5,817,033 A | 10/1998 | DeSantis et al. | |
| D424,194 S | 5/2000 | Holdaway et al. | |
| D441,077 S | 4/2001 | Garito et al. | |
| 6,231,552 B1 | 5/2001 | Jentzen | |
| 6,432,046 B1 | 8/2002 | Yarush et al. | |
| 6,613,010 B2 | 9/2003 | Castellano | |
| 6,616,448 B2 | 9/2003 | Friedman | |
| D483,116 S | 12/2003 | Castellano | |
| 6,689,095 B1 | 2/2004 | Garitano et al. | |
| 6,783,514 B2 | 8/2004 | Tovey et al. | |
| 6,824,526 B2 | 11/2004 | Castellano | |
| 7,018,356 B2 | 3/2006 | Wise et al. | |
| 7,419,472 B2 | 9/2008 | Hibner et al. | |
| 7,494,473 B2 | 2/2009 | Eggers et al. | |
| D615,192 S | 5/2010 | Mudd et al. | |
| 7,878,981 B2 | 2/2011 | Strother et al. | |
| D637,287 S | 5/2011 | Mudd et al. | |
| 8,029,460 B2 | 10/2011 | Rush et al. | |
| 8,066,629 B2 | 11/2011 | Dlugos | |
| 8,480,630 B2 | 7/2013 | Mudd et al. | |
| 8,603,028 B2 | 12/2013 | Mudd et al. | |
| 2002/0010433 A1 | 1/2002 | Johnson et al. | |
| 2002/0151843 A1 | 10/2002 | Correa et al. | |
| 2003/0144632 A1 | 7/2003 | Hommann et al. | |
| 2003/0199883 A1 | 10/2003 | Laks | |
| 2004/0092927 A1 | 5/2004 | Podhajsky et al. | |
| 2004/0147883 A1 | 7/2004 | Tsai | |
| 2005/0085767 A1 | 4/2005 | Menassa | |
| 2005/0131353 A1 | 6/2005 | Mossanen-Shams et al. | |
| 2005/0137496 A1 | 6/2005 | Walsh et al. | |
| 2005/0261633 A1 | 11/2005 | Khalaj | |
| 2006/0079765 A1 | 4/2006 | Neer | |
| 2006/0089594 A1 | 4/2006 | Landau | |
| 2007/0083155 A1 | 4/2007 | Muller | |
| 2007/0100363 A1 | 5/2007 | Dollar et al. | |
| 2007/0212385 A1 | 9/2007 | David | |
| 2007/0250010 A1 | 10/2007 | Hohlfelder et al. | |
| 2008/0033347 A1 | 2/2008 | D'Arrigo et al. | |
| 2008/0097325 A1 | 4/2008 | Tanaka et al. | |
| 2008/0108952 A1 | 5/2008 | Horvath et al. | |
| 2008/0188816 A1 | 8/2008 | Shimazaki et al. | |
| 2008/0200758 A1 * | 8/2008 | Orbay et al. | 600/112 |
| 2009/0088703 A1 | 4/2009 | Azar | |
| 2009/0124996 A1 | 5/2009 | Heneveld et al. | |
| 2009/0143746 A1 | 6/2009 | Mudd et al. | |
| 2009/0240200 A1 | 9/2009 | Heneveld et al. | |
| 2009/0299328 A1 * | 12/2009 | Mudd et al. | 604/506 |
| 2010/0069848 A1 * | 3/2010 | Alferness et al. | 604/151 |
| 2010/0152675 A1 | 6/2010 | McClintock | |
| 2010/0152679 A1 | 6/2010 | Tezel et al. | |
| 2010/0280488 A1 | 11/2010 | Pruitt et al. | |
| 2010/0282774 A1 | 11/2010 | Greter et al. | |
| 2011/0021905 A1 | 1/2011 | Patrick et al. | |
| 2011/0092916 A1 | 4/2011 | Tezel et al. | |
| 2011/0137286 A1 * | 6/2011 | Mudd et al. | 604/506 |
| 2011/0160674 A1 * | 6/2011 | Holmes et al. | 604/192 |
| 2013/0131632 A1 | 5/2013 | Mudd et al. | |
| 2013/0131633 A1 | 5/2013 | Mudd et al. | |
| 2013/0274670 A1 | 10/2013 | Mudd et al. | |

FOREIGN PATENT DOCUMENTS

| | | |
|---|---|---|
| EP | 1486218 | 12/2004 |
| EP | 1859827 | 11/2007 |
| EP | 1923086 | 5/2008 |
| EP | 2335755 | 6/2011 |
| FR | 2622457 | 5/1989 |
| WO | 99/48601 | 9/1999 |
| WO | 2005/095225 | 10/2005 |
| WO | 2008/019265 | 2/2008 |
| WO | 2008/079824 | 7/2008 |
| WO | 2009/098666 | 8/2009 |
| WO | 2009/158145 | 12/2009 |

OTHER PUBLICATIONS

Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641, XP004404219.

Wang et al., "In vivo stimulation of de novo collagen production caused by cross-linked hyaluronic acid dermall filler injections in photodamaged human skin.", Archives of Dermatology, American Medical Association, US, vol. 143, No. 2, Feb. 1, 2007, pp. 155-163, XP002574140.

* cited by examiner

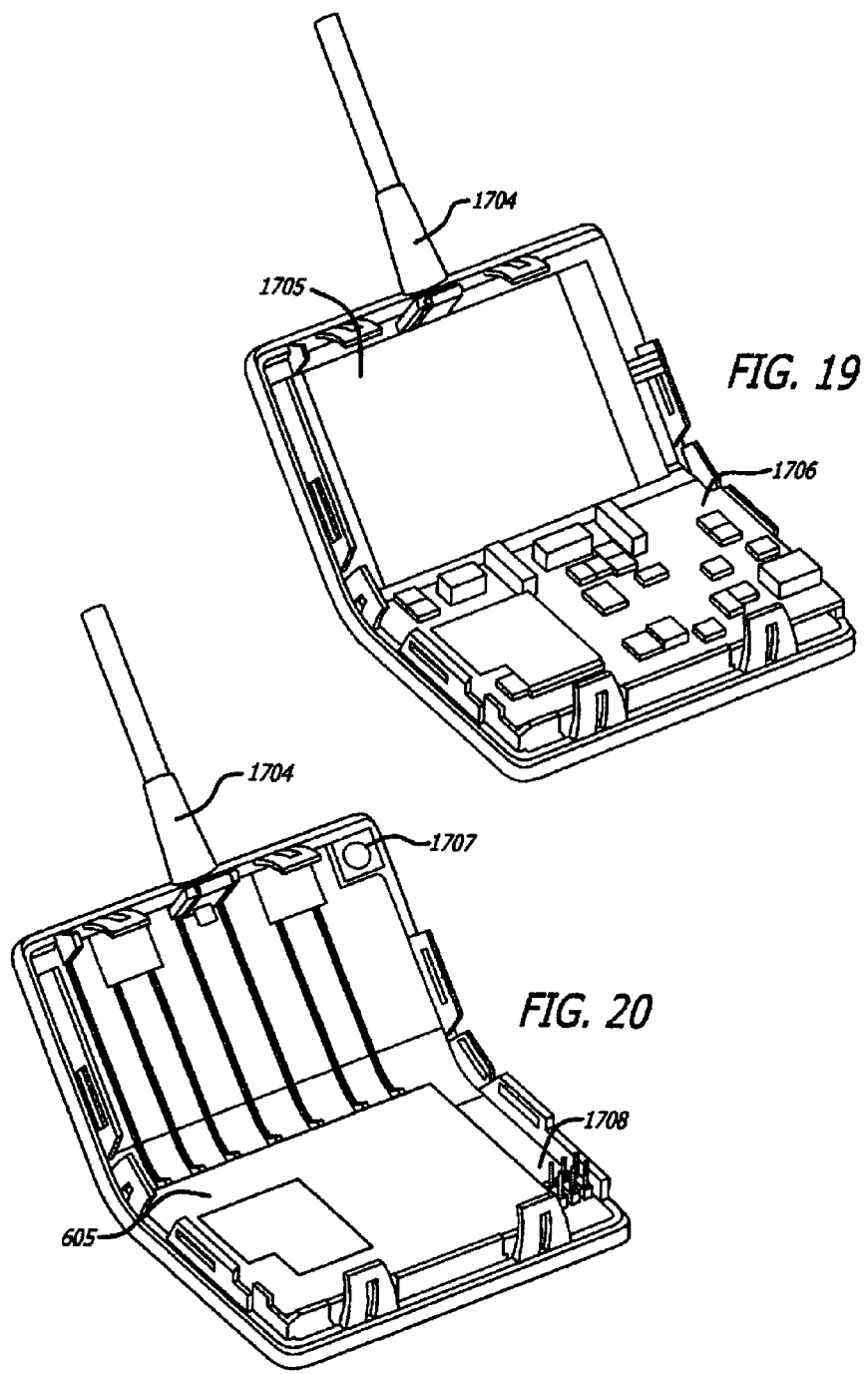

MODULAR INJECTION DEVICE

RELATED APPLICATION

This application is a continuation of U.S. patent application Ser. No. 13/111,731, filed May 19, 2011, which claims priority to U.S. Provisional Patent Application No. 61/346,354 filed on May 19, 2010, the entire disclosures of which are incorporated herein by this reference.

BACKGROUND

A number of medical and cosmetic applications involve the controlled injection of substances into the body.

A medical syringe is a simple piston pump consisting of a plunger that fits tightly in a cylindrical barrel. The plunger can be pulled and pushed along inside the barrel, allowing the syringe to take in and expel a fluid through an orifice at the distal open end of the barrel. The distal end of the syringe is typically fitted with a hypodermic needle to transdermally introduce the fluid in the barrel into the body of a patient. Syringes are often used to administer injections. Surprisingly, other than the materials used to make them, the typical, conventional disposable syringes used for administering the advanced injectable substances or medicaments of today, are much the same as the very earliest syringe designs.

Unfortunately, the classic syringe/needle system is far from optimal for the administration of today's injectable aesthetic compositions. Hydrogel-based dermal fillers can be quite difficult to inject using the conventional syringe/needle system or conventional injection techniques. Many dermal fillers are by their nature highly viscous, thus requiring relatively high extrusion forces, especially when injected through preferred fine gauge needles. Moreover, these materials are typically injected into the face to correct wrinkles, including fine wrinkles as well as other minor defects in skin, and are therefore must be sometimes injected in trace amounts, and always with very high precision. Interestingly, these dermal fillers are commonly introduced into skin using quite standard needle and syringe combinations.

Using a traditional syringe, physicians are required to supply possibly significant force, which may reduce the practitioner's ability to control the syringe. Further, traditional syringes typically require the user's hand to be placed a significant distance from the site of the injection in order to operate the plunger, which may also lead to inaccuracy. Automated injection machines, which supply the force required to perform the injection using a motor, may reduce some of these problems. However, some motorized injection devices have the disadvantage that they may be heavy and bulky, requiring, for example, a battery which may add significantly to the weight of the device. This added bulk and weight may lead to a lack of control because of user fatigue, etc.

Systems have been developed and described for facilitating injection of dermal fillers. One such system is described in Mudd, U.S. patent application Ser. No. 12/994,568, filed Jan. 24, 2011, commonly owned herewith, the entire disclosure of which being incorporated herein by this reference. Mudd describes a handheld, motorized dermal filler injector that is capable of dispensing viscous injectable material at a low flow rate, for example, in some instances, a flow rate of only 0.001 ml/sec, at the high pressures necessary to extrude the fluid though a fine gauge needle.

The present invention provides an improved system for injecting dermal fillers, or other materials into skin, for example.

SUMMARY

The present invention provides easy to use, highly accurate, programmable, user-friendly injection systems that have numerous benefits over conventional injection systems.

In one aspect of the invention, a modular injection system is provided which generally comprises a handheld injector unit including a grippable housing including a distal end having a coupling portion, and a drive unit contained within the housing, and a separate control unit, remote from the injector unit, the control unit including a controller/processor configured to control the drive unit. The system may further comprise a syringe or cartridge, couplable to the coupling portion of the grippable housing, and containing an injectable fluid, such as a hyaluronic acid-based dermal filler. The injector unit includes a movable plunger driven by the drive unit and is extendable in a distal direction to cause extrusion of the injectable fluid from the cartridge when the cartridge is coupled to the coupling portion.

Advantageously, the handheld injector unit component of the present invention is lightweight and easy to manipulate and grip. Many of the heavier components of the system are housed in the separate control unit. In some embodiments, the control unit includes a display, for example, a visual display screen for displaying useful information to the user, for example, amounts of fluid in the cartridge, amounts of fluid already dispensed from the cartridge, rate of injection of fluid, or other information. In some especially advantageous embodiments, the control unit is mountable to a user's arm or wrist to allow the user to view the display while operating the injector unit within the same field of vision.

In some example embodiments, the control unit may be powered by an electrical power source; and the handheld injector unit may draw electrical power from the power source using the cable. In other example embodiments, the control unit may further include a control unit body; a display in communication with the control unit; and an input device in communication with the control unit.

In some example embodiments, the input device may be configured to receive the user input indicating the injection rate; and the display may be configured to display the injection rate indicated by the user input. In still other example embodiments, the display may include a video display screen configured to display information indicating a volume of fluid injected.

In yet further example embodiments, the injector unit may further include a sensor configured to measure a physical parameter that is correlated with the volume of fluid injected; and the display may be configured to display the volume of fluid injected responsive to information received from the sensor.

In some example embodiments, the control unit may further include a wrist strap configured to attach the control unit to a user's wrist during use. In other example embodiments, a side of the control unit body may be shaped to conform to a user's wrist.

In another example embodiment, the control unit may further include a connector, disposed on the control unit body, configured to connect the control unit to the cable. In yet another example embodiment, the cable may be permanently attached to the control unit.

In still another example embodiment, the injector unit may further include an injector unit body; a syringe housing disposed at a proximal end of the injector unit body; a needle mount disposed at a proximal end of the syringe housing; and an input device configured to trigger an injection.

In some example embodiments, the drive unit may be configured to extrude fluid from a syringe disposed in the syringe housing, through the needle mount. In other example embodiments, the drive unit may be configured to cause a fluid to be extruded responsive to a user interaction with the input device. In further example embodiments, the input device is an inject button and the drive unit may be configured to stop causing the fluid to be extruded responsive to an indication that the inject button has been released.

In some example embodiments, the injector unit may further include a syringe loading door, hinged to the injector unit body, configured to allow loading of a syringe when the door is open.

In yet other example embodiments, the syringe housing may be transparent, configured to allow a user to view a syringe disposed within the housing.

In some example embodiments, the cable may be permanently attached to the injector unit.

In still other example embodiments, the injector unit may further include a connector, disposed on the injector unit body, configured to connect the injector unit to the cable.

Some example embodiments may provide a modular injection device, which may include a handheld injector unit including an injector unit body; a motor housed in the injector unit body and configured to apply an extrusion force to a fluid; a syringe housing disposed at a proximal end of the injector unit body and configured to hold a syringe; a needle mount disposed at a proximal end of the syringe housing; and a plunger configured to be driven into the syringe housing by the motor. The injection device may also include a control unit remote from the injector unit, configured to receive a user input indicating an injection rate and configured to control the motor responsive to the user input indicating the injection rate, the control unit which may include a control unit body; an electrical power source configured to supply electrical power to the control unit and the injector unit; a display in communication with the control unit; and an input device in communication with the control unit and configured to receive the user input. In addition, the injection device may include a cable configured to connect the control unit to the injector unit.

Further example embodiments provide a modular injection device, which include a handheld injector unit which may include an injector unit body; a drive unit housed in the injector unit body and configured to apply an extrusion force to a fluid; a syringe housing disposed at a proximal end of the injector unit body and configured to hold a syringe; a needle mount disposed at a proximal end of the syringe housing; a first wireless device; and a first electrical power source configured to supply power to the injector unit. The injection device may also include a control unit remote from the injector unit configured to receive a user input indicating an injection rate and configured to control the drive unit responsive to the user input indicating the injection rate, the control unit which may include a control unit body; a second wireless device configured to wirelessly communicate with the first wireless device; a second electrical power source configured to supply electrical power to the control unit; a display in communication with the control unit; and an input device in communication with the control unit and configured to receive the user input.

BRIEF DESCRIPTION OF THE DRAWINGS

The present invention will be more readily understood from a detailed description of example embodiments taken in conjunction with the following figures:

FIG. 19 illustrates exemplary internal components of the control unit illustrated in FIG. 17.

FIG. 20 illustrates further exemplary internal components of the control unit illustrated in FIG. 17.

DETAILED DESCRIPTION

As explained above, a number of medical and cosmetic procedures involve the controlled injection of liquids, gels, and other fluids. For instance, procedures involving the injection of botulinum toxin or the injection of dermal fillers, may require highly controlled injections. In such instances, it may be advantageous to perform the injection with an automated injection device. Using such devices, users need not supply the force which extrudes the injectable fluid though the needle themselves. Rather the device may supply that force, and may extrude the fluid at a user controller rate, leaving the user free to concentrate on the injection itself, e.g. positioning of the needle. Such devices, however, are typically significantly more bulky then traditional syringes, including control hardware, motors, power sources, etc. The additional size and weight may reduce user control, e.g. fatiguing the user, and increasing the distance between the user's hand and the point of the injection. Example embodiments may address such problems by providing modular injector devices designed to reduce the size and weight of the portion of the device which is held in the user's hand.

Figure 1:
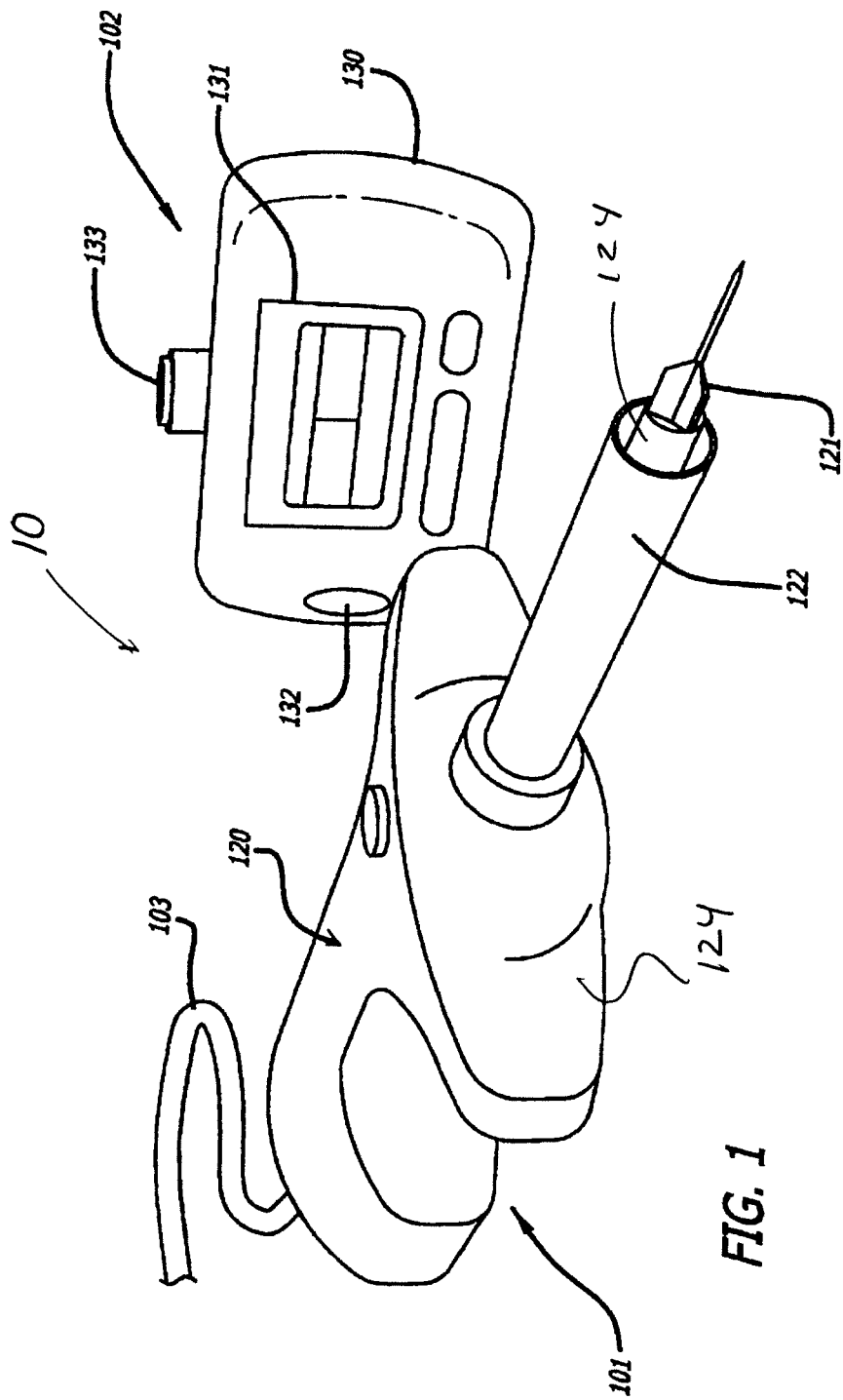
FIG. 1 illustrates an example injector device in accordance with an example embodiment.

Accordingly, dermal filler injector systems are provided, exemplary embodiments thereof being illustrated in FIG. 1. The system 10 may include a handheld injector unit 101 and a separate control unit 102. The two units 101 and 102 are in communication with each other. For instance, the units may be connected together wirelessly, or with a communication cable, a power cable, or both 103.

Figure 2:
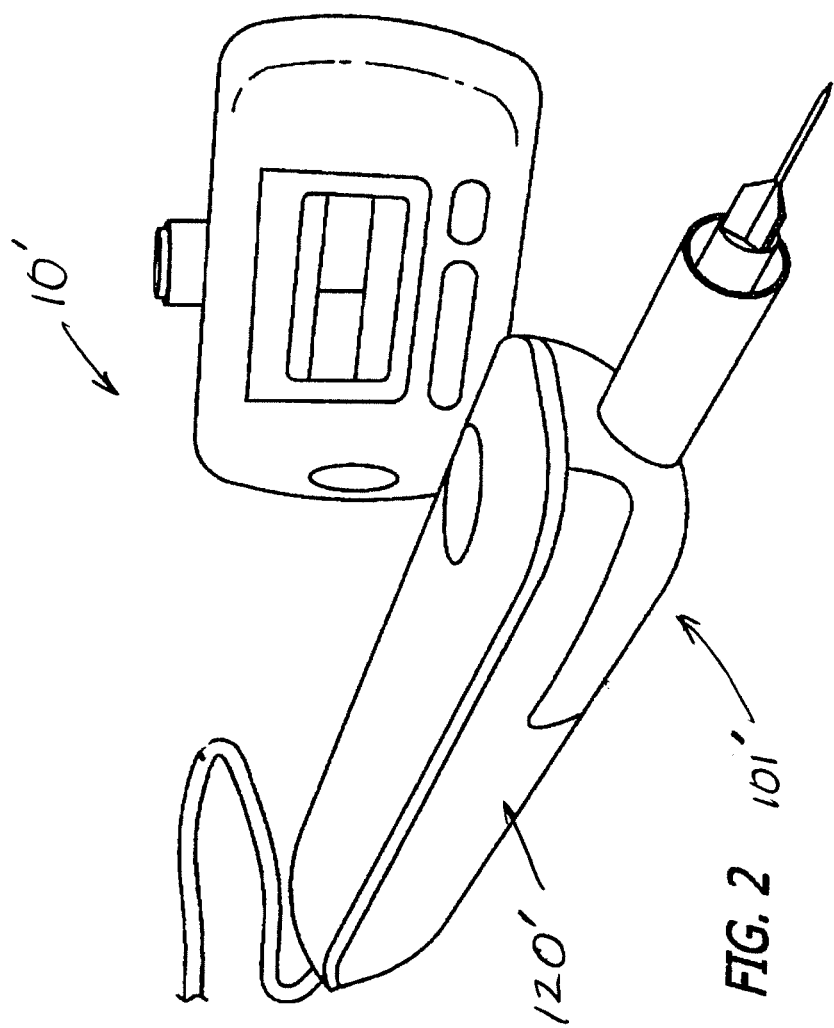
FIG. 2 illustrates another example injector device in accordance with an example embodiment.

The injector unit 101 may include a body 120 having a grippable housing 124, which may be made of any suitable material, e.g. metals, thermoplastics, thermoplastic elastomers (TPEs), silicones, glass, etc., or any combination of materials. The body 120 may be shaped to comfortably accommodate a user's hand. For instance, as shown in the figure, the body 120 may form a grip, which may allow a user to securely grasp the injector unit 101. As shown in FIG. 1, the body 120 itself may have one or more protrusions near a distal end of the injector unit body 120, which may, for example, prevent a user's hand from sliding forward when in use. Similarly, the injector unit body 120 may have one or more protrusions near a proximal end, which may prevent a user's hand from sliding backwards. In addition, a portion of the injector unit body 120 designed to be gripped may be textured to provide a secure grip, or may be covered in a layer of material designed to provide a secure grip. Another system 10' having an alternative injector unit 101' is shown in FIG. 2. In this particular design, the injector unit body 120' is more of a pen-style shape and will be discussed hereinafter with reference to FIG. 4. Injector unit 101' may be substantially identical to injector unit 101, except for the body shape and as discussed elsewhere herein.

Turning back to FIG. 1, the injector unit 101 may be designed to attach to and operate a standard needle and syringe combination. Alternatively, the injector unit 101 is designed to be couplable to a removable cartridge 121 having a needle though which the injectable material may be extruded. For instance, the injector unit 101 may provide any suitable attachment to cartridge 121, for example, a luer slip or luer lock attachment. The needle itself may have any suitable gauge, for example, a gauge between about 10 and about 33.

The injector unit 101 may provide a syringe housing 122 on which the cartridge 121 or syringe may be secured, although, in other embodiments, a needle is attached directly to the injector unit body 120 which houses a chamber containing a fluid to be injected. The syringe housing 122 may be, for example, substantially in the form of a tube, which may, at a distal end, connect to the injector unit body 120 and, at a distal end, connect to the needle mount 121. The syringe housing 122 may be designed to hold a syringe 123, for example a disposable, pre-filled syringe 123. The syringe housing 122 may be all or partially transparent, allowing a user to view the syringe 123 during operation. For example, the syringe housing 122 may provide a user with a view of both a syringe 123 in the housing and also a syringe plunger which may extrude fluid from the syringe 123 when the device is in operation.

Figure 3:
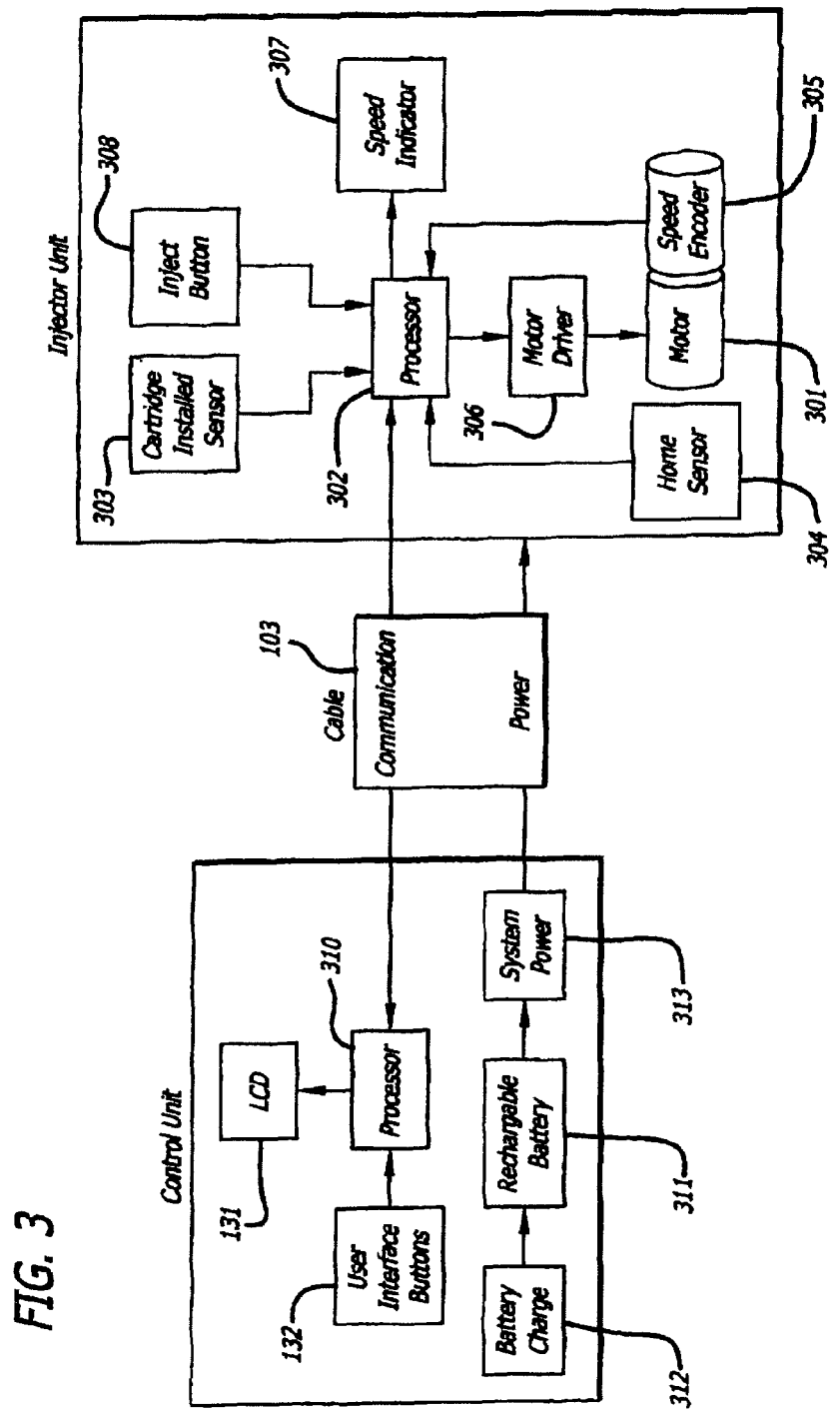
FIG. 3 illustrates a schematic view of an example injector device in accordance with an example embodiment.

The injector unit 101 may also contain an injection drive mechanism, as shown in FIG. 3. For instance, in injection drive mechanism may include a motor 301 which may be configured to push a syringe plunger through the syringe 123. As the syringe plunger moves through the syringe 123, the pressure exerted by the plunger may cause the material in the syringe 123 to be extruded through the needle 121. In other example embodiments, other drive systems may be used. For instance, some embodiments may use a pump to extrude the fluid, or may use pressurized syringes, controlling the injection with a valve, etc. The injection drive unit may be capable of delivering a force sufficient to extrude viscous and non-viscous liquids and gels through a needle 121 of standard size. For example, the injection drive mechanism may be capable of applying a force of up to about 100 N, and extruding material at a rate within a range of about 0.001 mL/sec to about 1 mL/sec. The syringe housing 122 may provide users with a view of the plunger in operation, over the entire length which the syringe plunger may travel during use.

In example embodiments, the motor 301 may be housed within the injector unit body 120. The motor 301 may be any suitable electric motor capable of supplying the necessary force. In addition, the motor 301 may be attached to a plunger via a drive mechanism, which may function to transfer the rotational motion of the motor 301 into the linear motion of the plunger. The plunger itself may also be housed within the injector unit body 120. When in operation, however, the plunger may extend into the syringe housing 122 and the syringe itself 123, causing the fluid in the syringe 123 to be extruded.

The injector unit 101 may also include a syringe retention and ejection mechanism. The mechanism may facilitate loading of, e.g., pre-filled, disposable syringes 123. The mechanism may also provide for the rotation of syringes 123. In example embodiments syringes may be loaded though a loading door.

Figure 4:
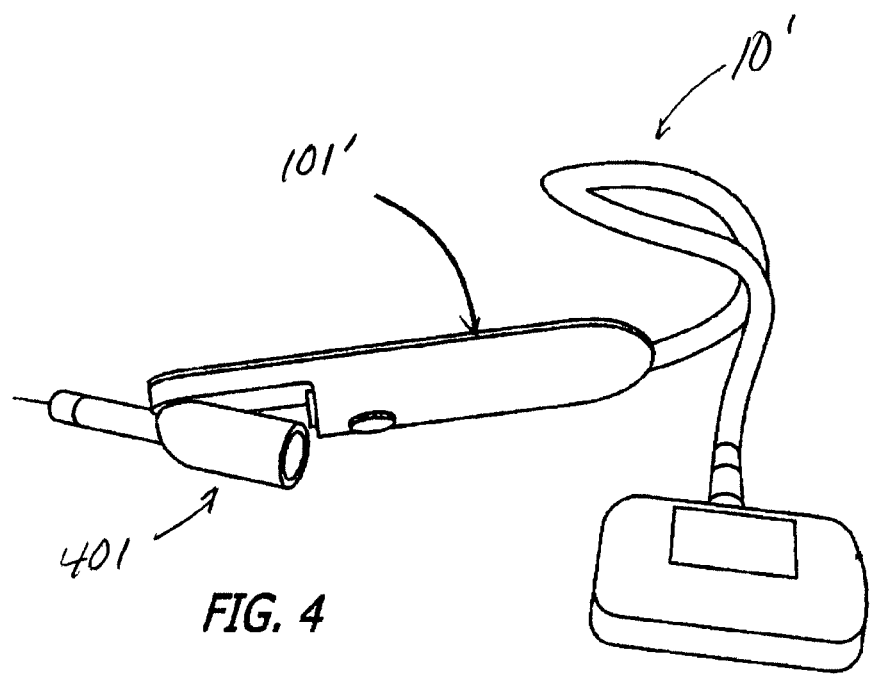
FIG. 4 illustrates an example injector device in accordance with an example embodiment.

For example, as illustrated in FIG. 4, the pen-style injector unit 101', discussed briefly hereinabove, may have a loading door 401 formed in the injector unit body 120. The door 401 may be hingedly attached to the body 120, e.g., near the distal end of the injector unit 101, and may rotate from a latched position, shown in FIG. 2, to an open position as shown in FIG. 4, to allow for the loading and ejection of fluid filled cartridges or standard syringes 123. The injector unit 101' may be fully sealed to prevent fluid from entering housing, for facilitating maintenance of the system 10'.

The injector unit 101 may contain a control system, seen in FIG. 3, which may be a portion of a control system for the entire device. For instance, the injector unit 101 may include a controller/processor 302 which may control the functioning of the injector unit 101 and may also facilitate communication with the control unit 102. The processor 302 may be any suitable processor unit of a kind normally used in such devices. Such a processor 302 may have an integrated memory and/or storage system or distinct memory or storage systems may be provided in the injector unit 101. In addition, the processor 302 may be in communication with other components which may be included in the injector unit 101.

For instance, the injector unit 101 may include a number of sensors. As illustrated, the injector unit 101 may include a syringe inserted sensor 303. Such a sensor 303 may detect whether a syringe 123 is inserted in the syringe housing 122. The syringe inserted sensor 303 may prevent the injector unit 101 from attempting to perform an injection without a syringe 123 properly loaded. The injector unit 101 may include other sensors as well. For example, as illustrated, the injector unit 101 may include a home sensor 304, which may detect whether the injector unit 101 is in a home state.

Further, the injector unit 101 may also include a rotation encoder 305. The rotation encoder 305 may be connected to the motor 301, and may be capable of sensing the rotation of the motor 301. For example, the motor 301 may rotate a portion of the encoder 305. The rotation encoder 305 may be an encoder of any suitable kind. The encoder 305 may be in communication with the processor 302 and may transmit state information to the processor 302, allowing the processor 302 to control the motor 301. Based on signals from the encoder 305, the processor 302 may be able to determine the position of the syringe plunger.

The injector unit 101 may also include a motor driver 306. The motor driver 306 may be in communication with both the processor 302 and the motor 301. The motor driver 306 may provide the systems necessary to control the operation of the motor 301. Based on input from the control unit 102, the sensors 303, 304, the encoder 305, etc., the processor 302 may direct the motor 301 through the motor driver 306, which in turn may control the extension of the plunger and thus the injection.

The injector unit 101 may also include a user feedback display 307, which may, in some embodiments, provide the user with information during the injection process. For instance, the display 307 may provide the total volume of fluid that has been injected up to that point in the process, the rate at which it is being injected, etc., or may display error indicators in the case of a malfunction.

The injector unit 101 may also include user input devices. For example, the injector unit may include an inject button 308. The inject button 308 may be located on the injector unit 101 in a position which is conveniently accessible by a user's fingers or thumb during injection. The inject button 308 may start and stop the injection process. For example, once the syringe 123 is loaded, and the control unit 102 is properly configured, the user may perform an injection with the injector unit 101. To do so, the user may press and hold the inject button 308 to begin the injection, and may release the button 308 to stop the injection. In other embodiments, the inject button 308 may work in other ways. For instance, the user may press the button 308 once to begin the injection and a second time to stop the injection. The inject button 308 may be in communication with the processor 302, which may control the injector unit 101 in response to a signal from the inject button 308.

The inject button 308 itself may be constructed of any suitable material and may take any usable form. In addition, like the door 401, the inject button 308 may be sealed. For instance, the injector unit 101 may include a seal disposed on the button 308 itself, or on the body 120 of the injector unit 101, etc., which may create a seal between the button 308 and the injector unit body 120.

The injector unit 101 may also be attached to a cable 103. For instance, a cable 103 may pass through an aperture formed in the injector unit body 120. The cable 103 may include multiple wires, including wires used for communication and power. The wires may connect to components housed in the injector unit 101. For instance, the power wires may attach to a power supply system, which may supply power to the motor 301, processor 302, and other components of the injector unit 101. The communication wires may connect to the processor 302. Connections may be made using any suitable technology. For instance, the wires may be soldered directly to components of the injector unit 101, or may be attached through connectors, etc. The cable 103 itself may be held in place by the injector unit body 120, and may form a seal with the injector unit body 120. In such a configuration, the cable 103 may be permanently attached to the injector unit 101. In other embodiments, however, the cable 103 need not be permanently attached. For instance, some example embodiments may provide a connector on or in the injector unit body 120, to which the cable 103 may be attached when in use.

The device may also include a control unit 102. The control unit 102 may, for example, also be portable. For instance, the control unit 102 may be designed to be strapped to the user's wrist via a VELCRO® strap or other typical strap or connector, or it can be attached to a chair, table or any surface. The strapping mechanism can be any mechanism known in the art, for example, a clasp, a buckle, a snap, a button, or the like. In other embodiments, the control unit 102 may not be portable, e.g. the control unit 102 may be a fixed unit into which the injector unit 101 may plug.

The control unit 102 may serve a number of functions, including providing power and electronic control signals through the cable 103 to the injector unit 101, which may, e.g. control and power the motor 301 of the injection drive mechanism.

As shown in FIG. 1, the control unit 102 has a control unit body 130, which may provide a housing for the control unit components 102. The control unit body 130 may be shaped to be comfortably strapped to a user's wrist, or arm. For example, a bottom side of the control unit 102 may be curved in order to conform to the shape of a user's wrist. As noted, the body 130 may also include a strap which may be used to attach the control unit 102 to a user, for instance a VELCRO® strap, or another kind of strap. In other embodiments, the control unit 102 may be shaped to attach to other places, for example, a table, etc. Further, in some embodiments, the shape described herein may be formed by one or more removable mounting pieces, which may be attached to the body 130 of the control unit 102, and which may be shaped to mount the control unit 102 to different objects, e.g. a user's wrist, a table, etc.

The control unit 102 may include an LCD screen 131, or other display, which may be located on a front of the control unit body 130, and which may allow a user to interact with the system. The display 131 may present a user with control information and may provide an interface, using which the user may control the operation of the device. For instance, as shown in FIG. 1, the display 131 may be configured to display a number of pieces of information, such as the volume of material that has been injected, the volume of fluid remaining in the syringe 123, the speed of the injection, battery charge, etc. In addition, other information may be displayed to facilitate different functions. For instance, the display 131 may also be configured to display configuration screens, or summary information, etc. In some example embodiments, the display can be in communication with, for example, the control unit and receive signals therefrom.

In addition, the control unit 102 may also include a keypad, or other input device, e.g. a dial, switch, etc. The keypad may include multiple buttons 132 which allow users to access and control the functions of the device. For example, the keypad buttons 132 may allow a user to control the speed and volume of the injection, or may allow the user to set other parameters related to the injection process. In addition, the control unit 102 may allow for other functions as well, for example, allowing a user to review historical use data, maintenance information, etc. The buttons 132 that make up the keypad may take any reasonable shape and configuration. For instance, as illustrated in FIG. 1, a number of buttons 132 may be provided on the control unit body 130, located generally around the display 131. In some embodiments the location of each button 132 may be coordinated with portions of the display screen 131. For example, if, as illustrated, injection speed is displayed at the bottom of the display screen 131, buttons 132 controlling the display speed may be located under the display 131. Of course, the buttons 132 provided may perform different functions based on context. In addition, in other embodiments the control unit 102 may be equipped with a touch screen.

As illustrated in FIG. 3, the control unit may have a processor 310, which may facilitate the functions of the control unit. The processor 310 may be connected to the input and output devices, for example, the display 131 and the keypad buttons 132. The processor 310 may be configured to provide a user interface using the display 131 and keyboard buttons 132. Further the processor 310 may be capable of sending signals to the injector unit 101, and receiving signals from the injector unit 101. Thus, the control unit 102 may send signals to the injector unit 102, which may, e.g., be used to control the motor's 301 rotation, based on the injection speed set using the control unit 102. In addition, the control unit 102 may receive signals from the injector unit 101, based on, e.g., information gathered by the encoder 305, which may allow the control unit 102 to calculate and display the volume of fluid injected, etc.

In addition, the control unit 102 may include a power system. For example, the control unit 102 may house a battery 311, or other power source, e.g. a rechargeable battery, fuel cell, etc., which may be located inside the control unit body 130. In one embodiment, the power is electrical power. The battery 311 may provide power to the control unit 102 and to the injector unit 101, via the cable 103. The battery 311 may be connected to the control unit 102 in any reasonable manner. For example, the battery 311 may be permanently connected, e.g. soldered, or may be connected through a connector. In the later case, a door may be provided in the control unit body 130, which may allow access to the battery 311 for removal and replacement. As the battery 311 is typically a significant part of the overall weight of such a system, providing the battery 311 in the control unit 102, reduces the weight of the injector unit 101, and thus may improve user control.

In addition, the control unit 102 may include a battery charger 312. The battery charger 312 may be capable of charging the battery 311 when connected to an external source of electricity. For example, the control unit 102 may include a connector, which may allow the control unit 102 to connect to a source of electrical power, such a standard 120 or 240 V AC power source. Of course, the control unit 102 need not connect to such a power source directly. Rather the control unit 102 may connect to a power adaptor or supply system, which may in turn connect to the primary power source. In addition, any suitable connector may be provided, e.g. in the body of the control unit 102, for connection to the external power source. In some embodiments, the same connector may be used to connect the control unit 102 to the cable 103 when in use.

Figure 5:
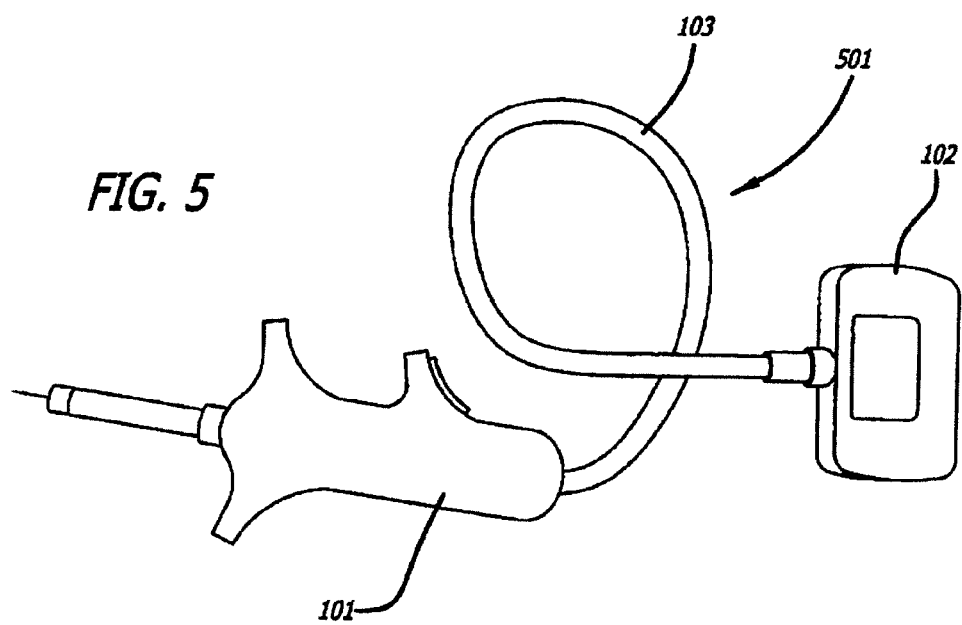
FIG. 5 illustrates an example injector device in accordance with an example embodiment.

As noted, the control unit 102 may be in communication with the injector unit 101 via the cable 103. Thus, the control unit 102 may provide a connector 133 using which the cable 103 may connect to the control unit's 102 systems. For instance, as illustrated in FIG. 1, a connector 133 may be provided at the top of the control unit 102, though the connector 133 may be placed in any suitable location. The connector 133 may be designed to connect securely with a complementary connector 501 attached to the end of the cable 103, as shown in FIG. 5. In order to ensure that the cable 103 does not separate during use, a locking mechanism may be provided, which secures the connection when engaged. In other embodiments, however, the cable 103 may be permanently attached to the control unit 102.

It is noted that, in other example embodiments, a cable need not be used. For example, in some example embodiments the injector unit 101 may be in wireless communication with the control unit 102 during use. For instance, each unit 101, 102 may include a wireless device, e.g. transmitter and receiver, which may be of any suitable type. During use, a communication channel may be established between the injector unit 101 and the control unit 102, using the wireless devices. Once established, the wireless communication channel may be used to exchange information and control signals between the units 101, 102 as it would be exchanged using an embodiment with a cable. Because wireless communications have a greater chance of being disrupted than communications over a cable, the injector unit 101 may be configured to react if wireless communication should be lost. For instance, the injector unit 101 may poll the control unit 102 periodically to sense whether it is in wireless communication with the control unit 102. Should a poll fail, the injector unit 101 may be configured to stop operation, to continue operation using locally stored configuration parameters, to activate an alarm, etc.

In a system using a wireless communication channel, the injector unit 101 may also include a power source, for example a battery, fuel cell, etc. In addition, the injector unit 101 may include the systems necessary to maintain the power source. For example the injector unit 101 may include a battery charger, and may be equipped to connect to an external power source.

In addition, some example embodiments may support both wireless and cabled communication. For instance, the injector unit 101 and control unit 102 may each include wireless devices and cable connectors. In such embodiments, the wireless devices may not be used when the units 101,102 are connected via cable. In addition, the injector unit 101 may be configured to house an optional power source. For example, the injector unit 101 may be configured to draw power over a cable, when attached the control unit 101 via cable. In this case, the optional power source need not be installed in the injector unit 101, reducing the weight of the unit. However, should the wireless devices be used for communication instead of the cable, the optional power source may be installed in the injector unit 101, which may be configured to draw power directly from the power source when in that configuration.

As with the injector unit 101, the control unit 102 may be sealed in order to allow for wipe down cleaning. For instance, seals may be provided for the cable connector 133, the buttons 132, and any other location where the control unit body 130 may open.

Figure 6:
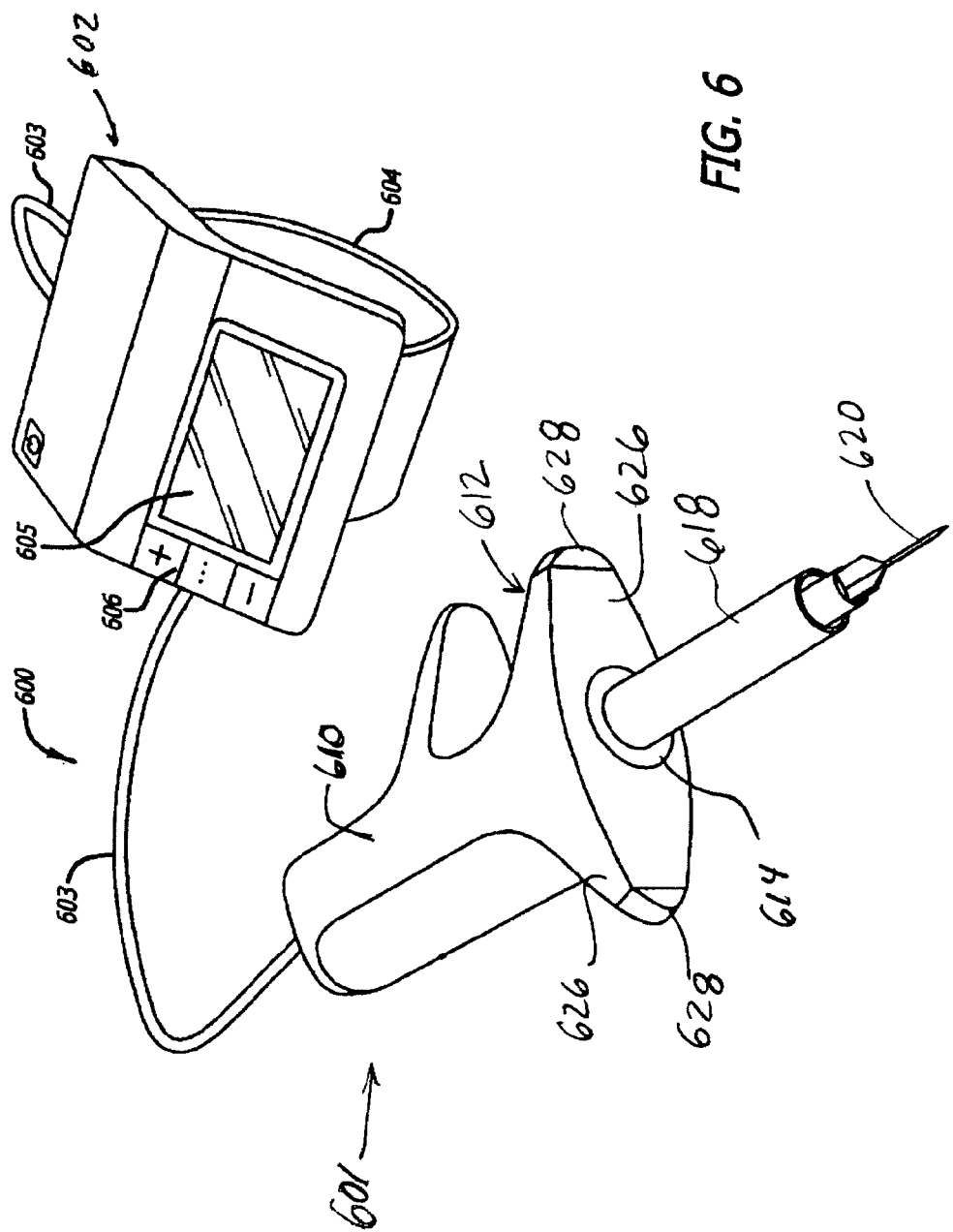
FIG. 6 illustrates an exemplary injection system in accordance with an example embodiment.

An exemplary system 600 according to the present description is illustrated in FIG. 6. System 600 generally includes, for example, injector unit 601, including an internal drive unit (not shown in this FIG) and separate control unit 602 remote from the injector unit 601. The control unit 602 includes a controller/processor such as described elsewhere herein, configured to control the drive unit. The injector unit 601 and control unit 602 are in communication with one another, for example, are electrically connected by line or wire 603. Control unit 602 includes strap 604 which allows connection to a user's wrist. Control unit 602 further includes a bank of control buttons 606 for controlling functions of the system through, for example, a menu driven system displayed on LCD screen 605.

The injector unit 601 includes a grippable housing 610 having an enlarged distal end 612 a having a coupling portion 614.

The system 600 may further includes a cartridge 618 sealingly couplable to the coupling portion 614 of the grippable housing 610, and containing an injectable fluid. The cartridge 618 may be fitted with a needle or cannula 620 of a suitable gauge. In this embodiment, the injector unit 610 includes a movable plunger (not visible in FIG. 6) driven by the drive unit and extendable in a distal direction, into the cartridge 618, to cause extrusion of the injectable fluid from the cartridge 618, for example, out of the distal tip of the needle 620, when the cartridge 618 is coupled to the coupling portion 614. In the embodiment shown, the enlarged distal end 612 is defined by substantially opposing, laterally extending flanges 626. The injector unit 601 includes substantially opposing ejection buttons, or triggers 628, configured to enable ejection of the cartridge from the coupling portion 614, for example, by simultaneous pressing of the triggers 628 by the user. As shown, each flange 626 includes one of the substantially opposing triggers 628.

Figure 7:
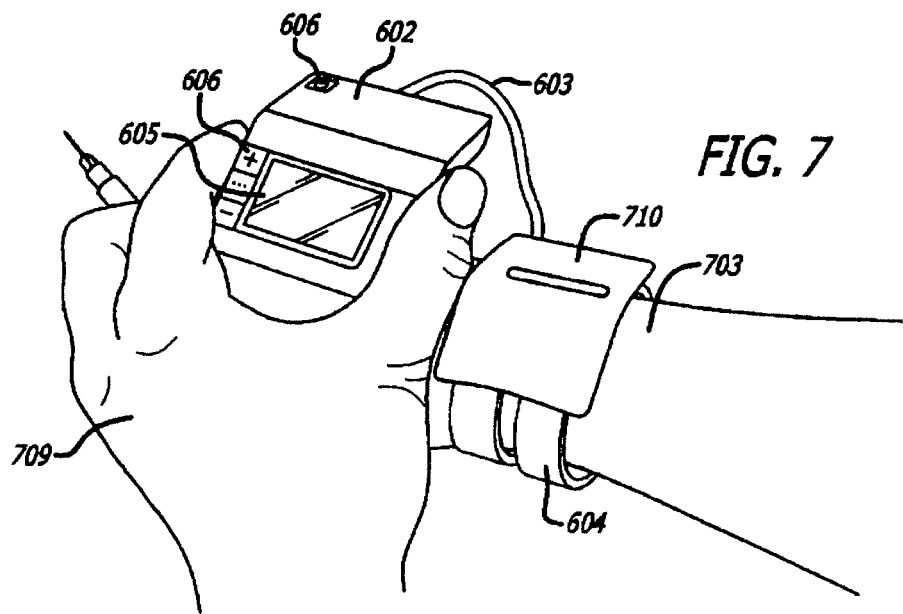
FIG. 7 illustrates how to use the system illustrated in FIG. 6.
Figure 8:
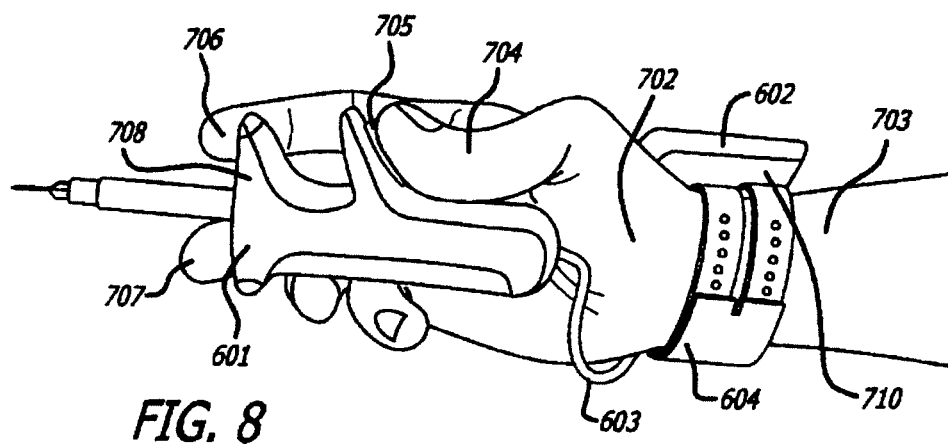
FIG. 8 also illustrates how to use the system illustrated in FIG. 6.
Figure 9:
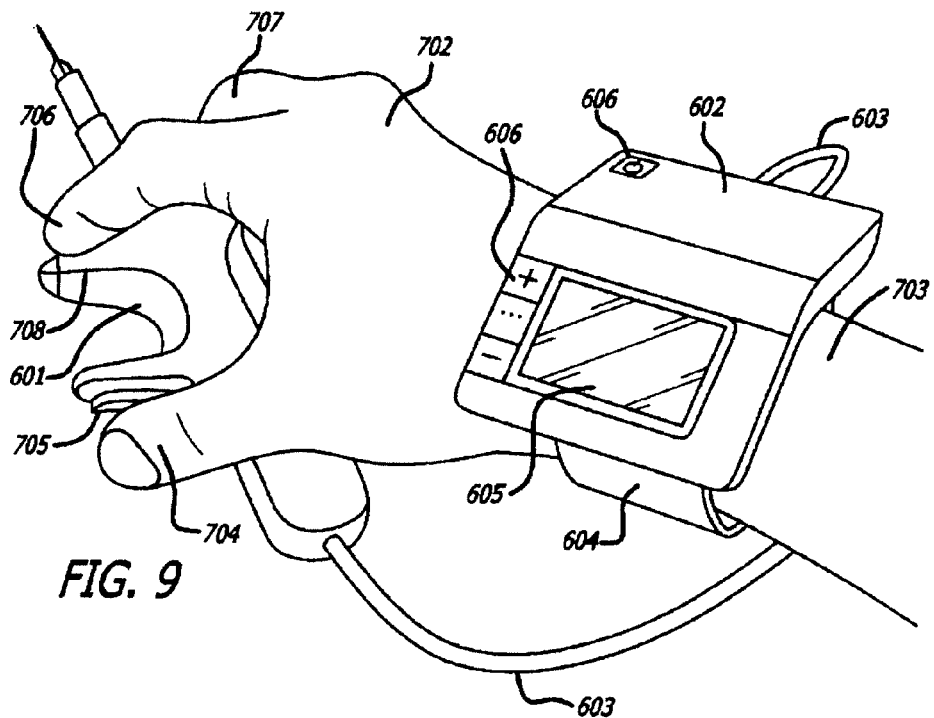
FIG. 9 again illustrates how to use the system illustrated in FIG. 6.

System 600 can be used as illustrated in FIGS. 7-9. For example, system 600 is used as a right-handed system, meaning injector unit 601 is handled in the right hand 702 and controller unit 602 is strapped to the right wrist 703. In other embodiments, the system can be a left handed system. Injector device 601 is held in right hand 702 such that first digit 704 rests on or near injection button 705. Second digit 706 and third digit 707 rest comfortably on top portion 708 of injector device 701. Left hand 709 is used, for example, to drive bank of control buttons 606 or to detach control unit 602 from base 710 attached to strap 604. It can be appreciated from FIG. 9, that the control unit 602, mountable to a user's arm or wrist, allows the user to view the control unit 602 while operating the injector unit 601 within the same field of vision.

Figure 10:
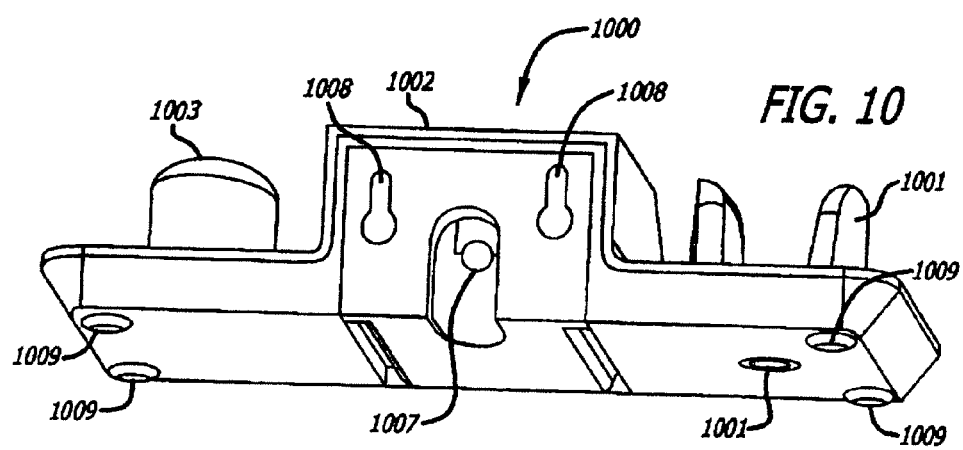
FIG. 10 illustrates a back view of a base station for housing an unused system illustrated in FIG. 6 according to an example embodiment.
Figure 11:
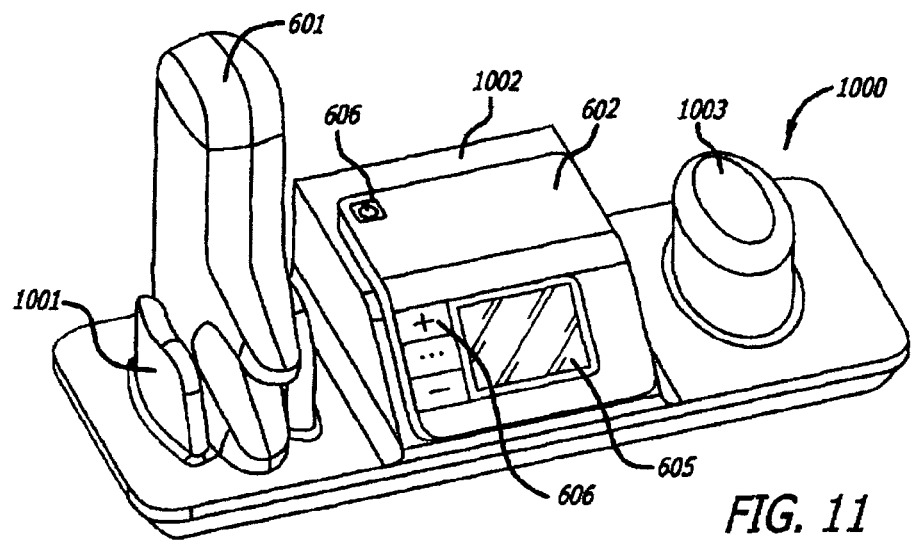
FIG. 11 illustrates a top perspective view of a base station housing an unused system illustrated in FIG. 6.
Figure 12:
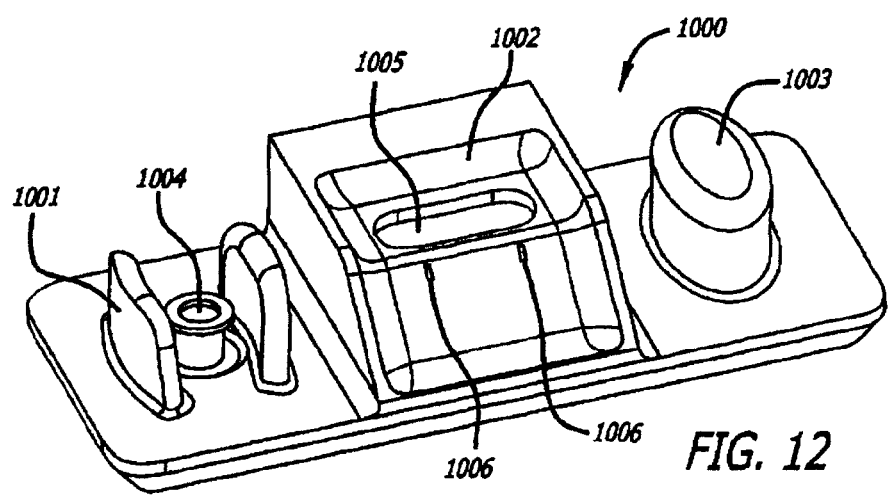
FIG. 12 illustrates a top perspective view of an empty base station as illustrated in FIG. 6.

In another embodiment, system 600 can be used with base station 1000, illustrated in FIGS. 10-12. Base station includes injector unit 601 storage slot 1001, control unit 602 charging dock 1002, and strap 604 post 1003. Storage slot 1001 includes removable cleaning plug 1004 which can be removed from base station 1000 and attached directly to injector unit when the injector unit needs cleaning. Charging dock 1002 includes plate 1005, or alternately individual magnets, and charging contacts 1006 used to charge control unit 602. Base station 1000 further includes port 1007 which can accommodate, for example, a power cable to charge injector unit 601 and/or control unit 602 and/or transfer data to or from either device. Base station 1000 can be wall mounted using wall mount slots 1008 or can be placed on a tabletop assisted by cushions 1009.

Figure 13:
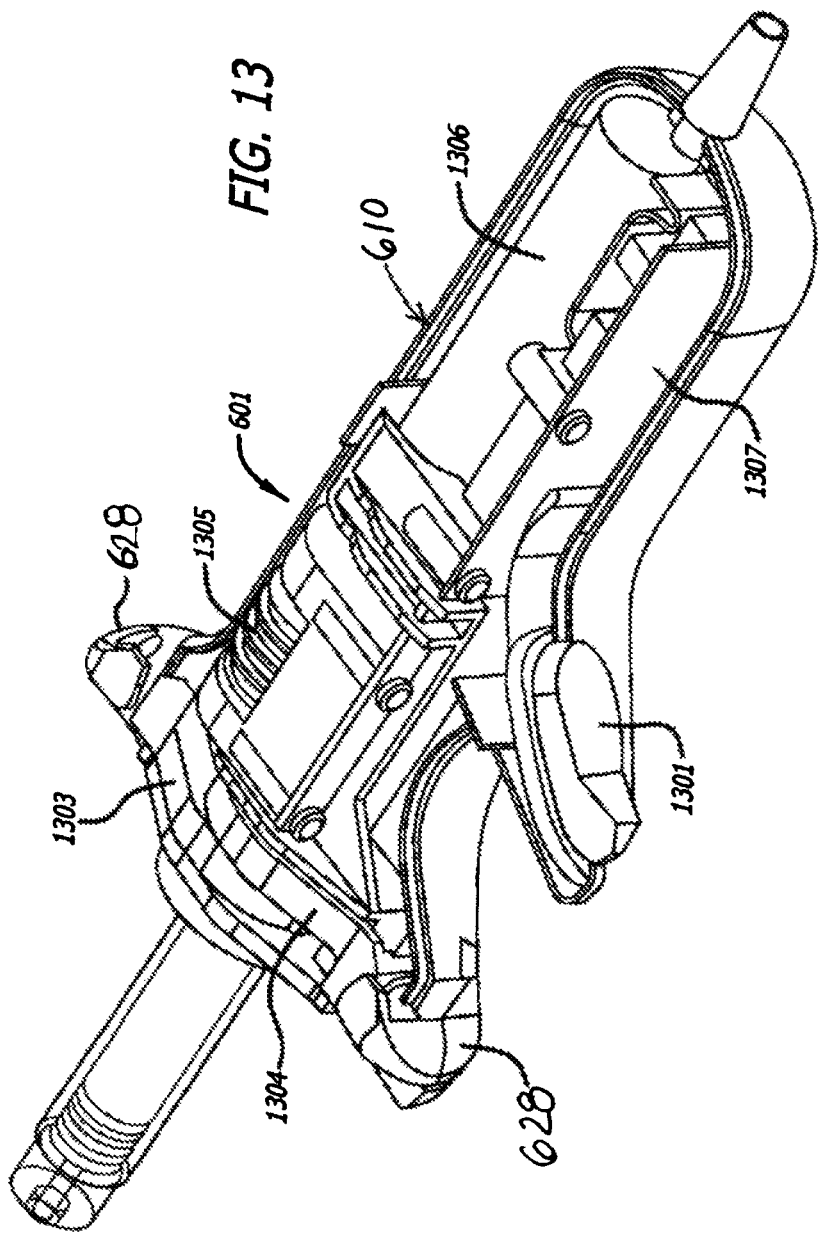
FIG. 13 illustrates the internal components of an example injector device.
Figure 14:
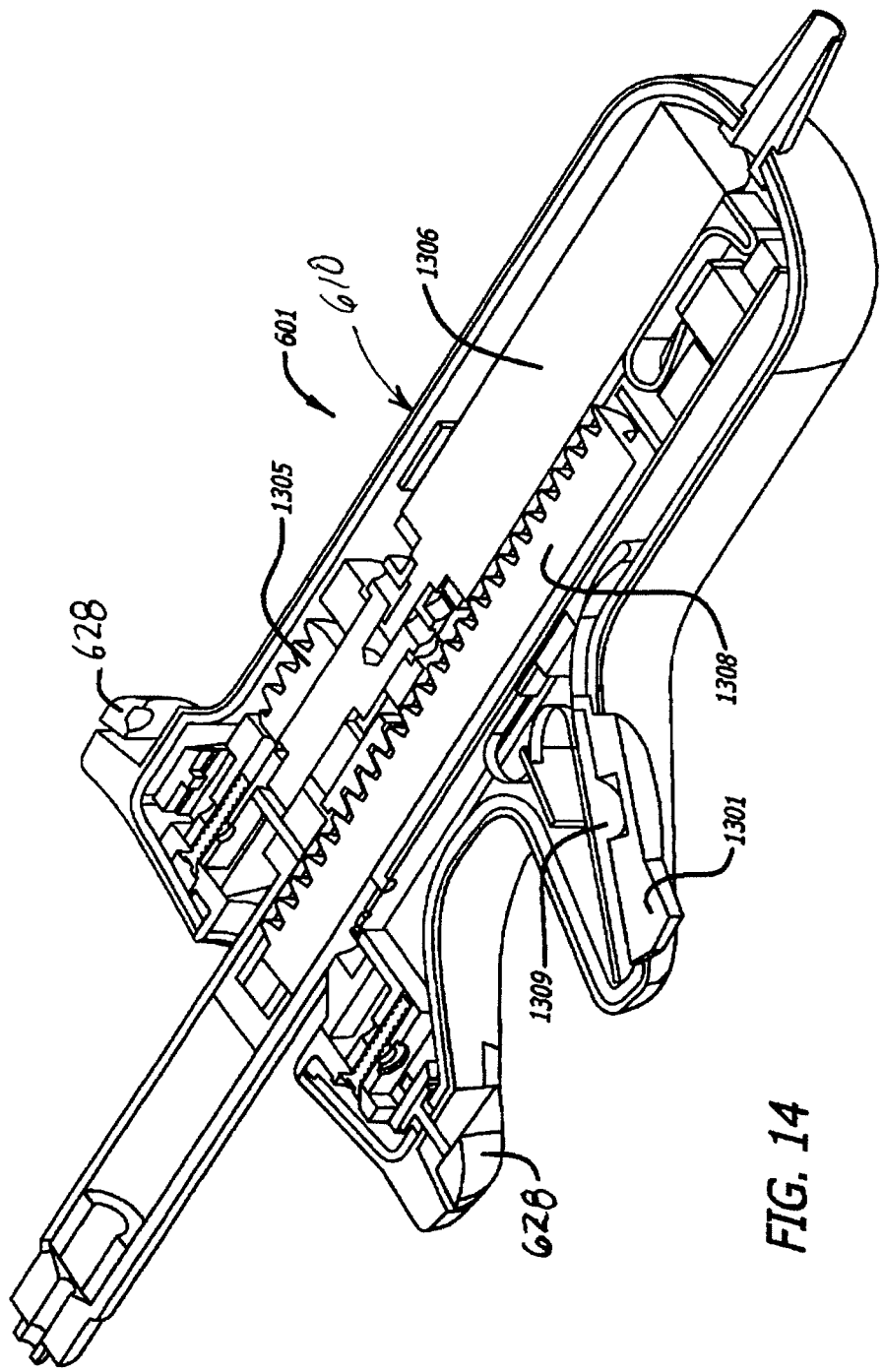
FIG. 14 further illustrates the internal components of an example injector device.
Figure 15:
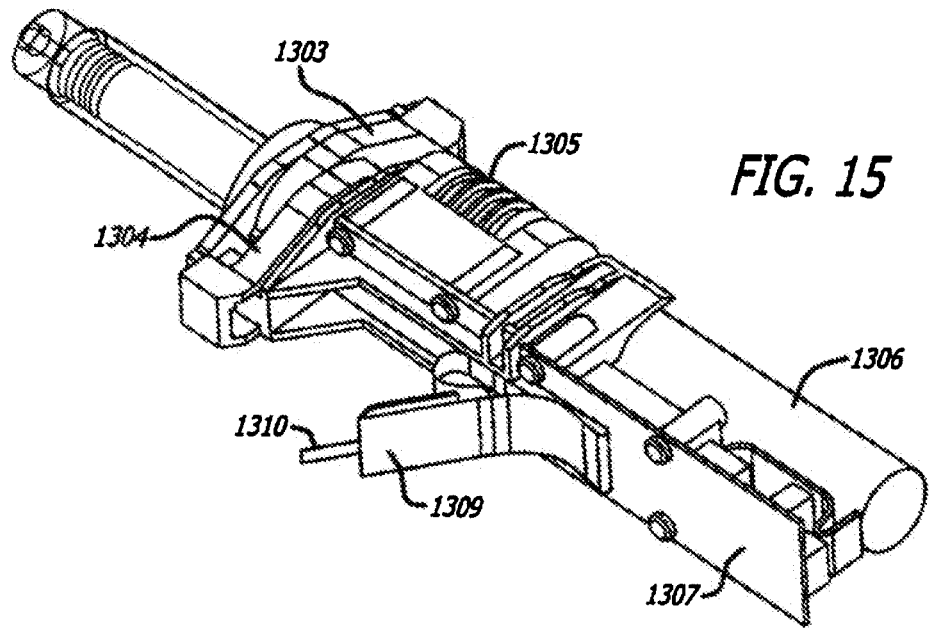
FIG. 15 further illustrates the internal components of an example injector device.
Figure 16:
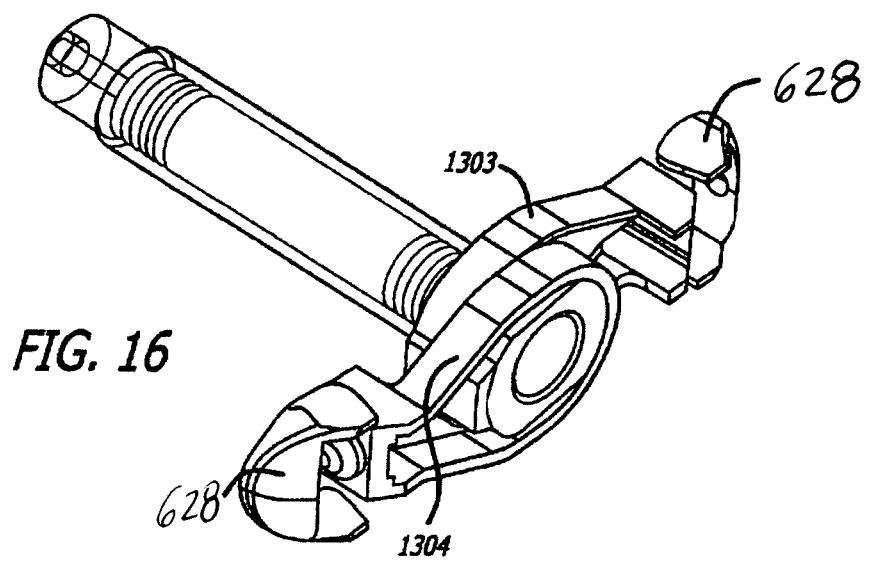
FIG. 16 illustrates an example retention mechanism.
Figure 17:
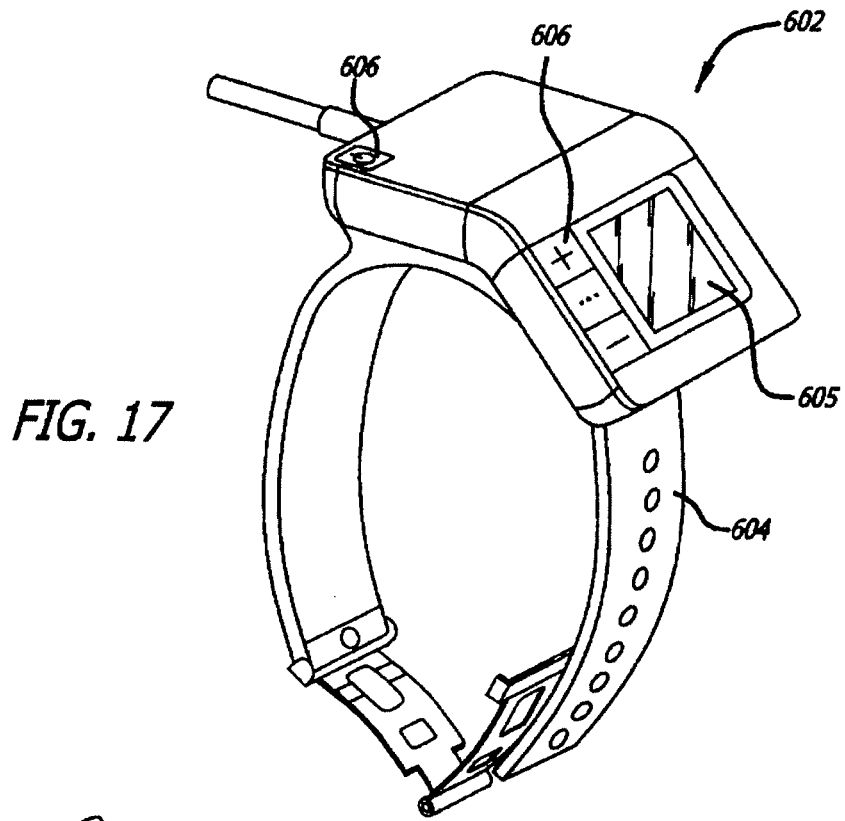
FIG. 17 illustrates an example control unit.
Figure 18:
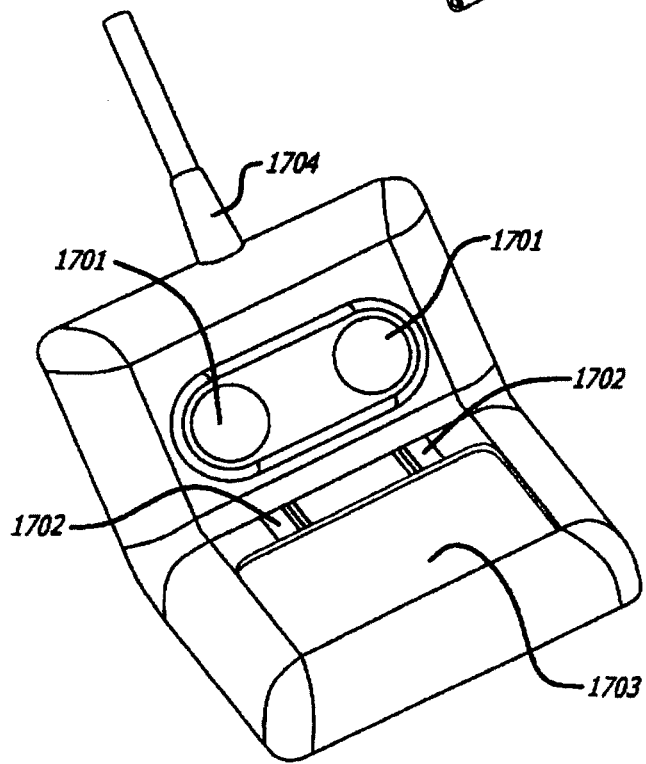
FIG. 18 shows a back view of the control unit illustrated in FIG. 17.

Exemplary internal components of injector device 601 are illustrated in FIGS. 13-16. Injector unit 601 includes inject button 1301 and cartridge eject buttons 628. FIG. 13 further illustrates first retention mechanism 1303 and second retention mechanism 1304 which hold a cartridge in place until it is ejected. Drive screw 1305 is driven by motor 1306 and controlled by circuit board 1307. Drive screw 1305 further drives movable plunger 1308 and inject button 1301 actuates pressure sensitive button 1309 as illustrated in FIG. 14. The movable plunger 1308 may be extendable beyond the distal end of the injector unit housing 610 to move fluid in the cartridge distally.

Optionally, injector device 601 can include LED indicators (not shown) for indication of injection speed. Injection speed can be indicated on injector device 601 or control unit 602 by, for example, with one or more LED indicators or other illuminating indicators.

Non-limiting internal components of control device 602 are illustrated in FIGS. 17-20. Control device 602 includes magnets 1701 which hold the unit to strap 604 or charging dock 1002. Charging contacts 1702 allow unit charging by contact with, for example, charging contacts 1006 on base station 1000. Information about the device, for example, model number, serial number and the like can be placed at label position 1703.

FIG. 19 further illustrates strain relief 1704 which prevents flexural strain on cable 103 (a strain relief can also be included on injector device 601). Battery 1705 is housed just below magnets 1701 within the unit. Control of the unit itself is accomplished using printed circuit board 1706 which is housed opposite battery 1705. Further included in control unit 602 are power button contact 1707, LCD screen 605, and capacitance sensing board 1708.

EXAMPLE

Figure 21:
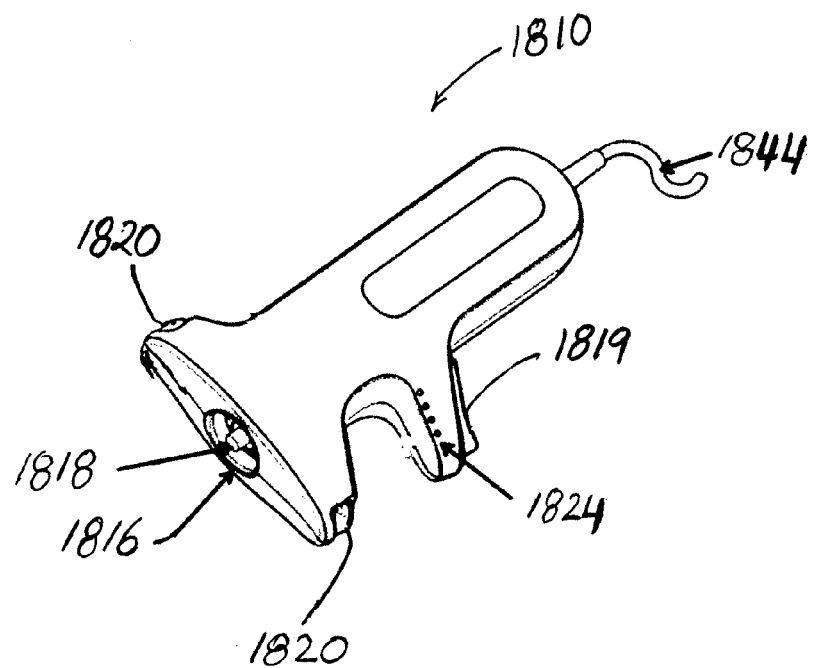
FIG. 21 is a perspective view of an injector unit component of a system in accordance with an exemplary embodiment of the invention.

Modular Injector System in Accordance with an Embodiment of the Invention Injector Unit The injector unit 1810 is a hand held a syringe-like device, as shown in FIG. 21, and it is compatible with specially designed 2 mL cartridges 1812 (shown in FIG. 23) containing a hyaluronic acid based dermal filler. The injector unit 1810 includes a cartridge slot 1816 that houses proximal end of the cartridge 1812. A plunger rod 1818 inside the cartridge slot 1816 is electromechanically moved forward inside the injector unit 1810 to extrude the cartridge contents when inject button 1819 is pressed. Eject buttons 1820 are provided for ejecting a spent cartridge. LED lights 1824 on the injector unit light up according to the extrusion rate during use. One, two, three or four lights illuminate which correspond to very low, low, medium, and fast extrusion rates.

Wrist Unit

Figure 22:
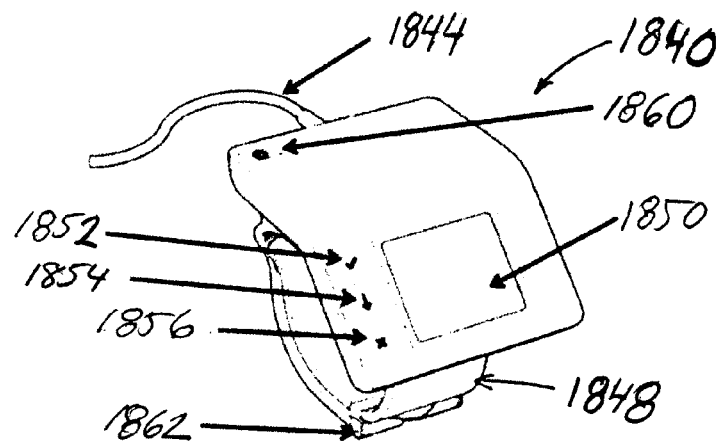
FIG. 22 is a perspective view of a control unit component of a system in accordance with an exemplary embodiment of the invention.
Figure 23:
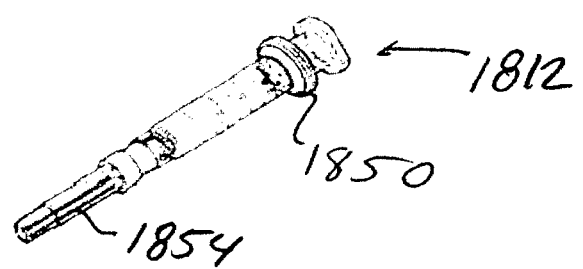
FIG. 23 is a perspective view of a cartridge and needle component of a system in accordance with the invention.

The control unit 1840, shown in FIG. 22, contains a battery and houses the software which controls the extrusion speed of the dermal filler from the cartridge 1812 (FIG. 23). It is permanently connected to the injector unit 1810 by a cable 1844. The wrist unit 1840 includes a display screen 1850, "OK/Yes" button 1852, "Scroll" button 1854, "No/Cancel/Exit" button 1856 and power button 1860. The control unit 1840 attaches magnetically to a wrist strap 1862.

Cartridge

The 2 mL cartridge 1812 for containing an injectable fluid such as a dermal filler, for example, Juvéderm Ultra Plus XC gel formulation, available from Allergan, Irvine, Calif., is shown in FIG. 23. The cartridge 1812 is made of cyclic olefin copolymer (COC). The cartridge 1812 includes a cartridge ring 1850, which seals the cartridge 1812 into the cartridge slot 1816 of the injector unit 1810. In this exemplary embodiment, the cartridge 1812 does not include a plunger or finger grips and cannot be used apart from the injection unit 1810. The cartridge 1812 is provided with a 30 G×¾" needle 1854.

The system, including injector unit 1810, control unit 1840 and cartridge 1812, is capable of extruding Juvéderm gel at 4 preset speeds: very low, low, medium and high. A fifth, dynamic speed, setting is available which allows injection of the entire range of speeds, from very low to high, depending on the amount of pressure exerted on the "Inject" button of the Injector Unit. Lighter pressure on the "Inject" button of the Injector Unit will correspond to a lower injection speed and higher pressure will correspond to a higher injection speed. The approximate corresponding flow rates are shown in the Table 2.

These flow rates were determined based on evaluating physician's typical extrusion rates.

TABLE 2

Injection Rates

| Speed Setting | Injection Rate (mL/minute)* |
|---|---|
| Very Low | 0.30 |
| Low | 0.60 |
| Medium | 0.90 |
| High | 1.20 |
| Dynamic | 0.30-1.20 |

*APPROXIMATE INJECTION RATE

Although the present disclosure has described the inventive injector system generally as being especially advantageous for administration of dermal fillers, it is to be appreciated that the system is also useful for injection of other substances. For instance, systems of the present invention may be used to administer agents such as botulinum toxin, an injectable substance, which is used for cosmetic and medical purposes. For example, a controlled quantity of botulinum toxin must be injected into a patient's body in a controlled, precise manner, often in very small amounts. The required precision and accuracy may be achieved using an example injector device according to the invention.

For example, a patient may seek treatment for a medical condition, e.g. blepharospasm ("excessive blinking"), from a qualified physician. In some cases, the condition may be treated with a controlled injection of a substance, in the example case, a controlled injection of botulinum toxin into the muscle tissue to be treated. In order to perform such an injection, the physician may use an example injector device described herein. For example, the physician may strap a control unit to his or her wrist. The physician may then attach the cable of an injector unit to the control unit, and may use the control unit to configure the system. For instance, the physician may select an injection speed using the control unit and may select other parameters.

The user may then load a syringe into the injector unit. For instance, the physician may select a pre-filled syringe filled with botulinum toxin, which may be inserted into the injector unit using a loading door. Once loaded, the physician may also attach a needle to the injector unit. For instance, the physician may select an appropriate needle for the given procedure and may attach that needle to the injector unit, e.g. using a luer lock connection.

The injector unit may then be ready for use. The physician may proceed to identify an area of the patient's body for injection. For instance, the physician may locate a muscle which may be causing the patient discomfort. The physician may then insert the needle into the desired location and may depress the inject button. When the inject button is depressed, the motor in the injector unit may turn, driving a plunger into the syringe and extruding the material in the syringe through the needle, at a rate controlled by the parameters selected using the control unit.

While the injector unit is extruding material, the control unit may display information relating to the injection process. The injector unit may also display information relating to the injection process, for example, but not limited to, LEDs that illuminate sequentially as the injection rate increases. For example, the user may be able to read the quantity of material injected off the display. Once the desired amount has been injected, the physician may release the inject button, stopping the injection process, and remove the needle from the patient. If another location is to be injected, and sufficient material remains, the process may be repeated, until material has been injected into all of the areas to be treated, or the syringe has been emptied.

The used syringe may then be removed from the device and discarded, along with the needle. The control unit may be disconnected from the injector unit, and both units may be cleaned. In other embodiments, the control unit and injector unit may be permanently attached to each other. In addition, the control unit may be plugged into a power source to recharge the battery if necessary.

In the preceding specification, the present invention has been described with reference to specific example embodiments thereof. It will, however, be evident that various modifications and changes may be made thereunto without departing from the broader spirit and scope of the present invention. The description and drawings are accordingly to be regarded in an illustrative rather than restrictive sense.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A modular injection system for administration of injectable fluids, the system comprising:
   a handheld injector unit including a grippable housing including a distal end having a coupling portion, and a drive unit contained within the housing;
   a wrist strap;
   a separate portable control unit, remote from the injector unit, the control unit including a controller/processor configured to control the drive unit and configured to be secured to the wrist strap; and
   a cartridge, couplable to the coupling portion of the grippable housing, and containing an injectable fluid;
   the injector unit including a movable plunger driven by the drive unit and extendable in a distal direction to cause extrusion of the injectable fluid from the cartridge when the cartridge is coupled to the coupling portion.

2. The system of claim 1 wherein the control unit further includes an input device configured to receive user input to program the controller/processor to set an injection rate for the fluid from the cartridge.

3. The system of claim 1 wherein the control unit is removably connectable to the wrist strap.

4. The system of claim 3 wherein the control unit is removably connectable to the wrist strap by magnetic elements.

5. The system of claim 1 further comprising a charging dock configured to receive both the injector unit and the control unit.

6. The system of claim 1 further comprising a cable connecting the control unit to the injector unit.

7. The system of claim 1 wherein the injector unit includes substantially opposing triggers configured to enable ejection of the cartridge from the coupling portion.

8. The system of claim 7 wherein the injector unit housing includes an enlarged distal end defined by substantially opposing, laterally extending flanges and each flange includes one of the substantially opposing triggers.

9. The system of claim 1 wherein the cartridge includes a cartridge ring sealingly engagable with the coupling portion.

10. The system of claim 1 wherein the movable plunger is extendable beyond the distal end of the injector unit housing.

11. The system of claim 1 wherein the control unit is mountable to a user's wrist to allow the user to view the control unit while operating the injector unit within the same field of vision.

12. A modular injection system for administration of injectable fluids, the system comprising:
    a handheld injector unit including a grippable housing including a distal end having a coupling portion, and a drive unit contained within the housing,
    a separate portable control unit, remote from the injector unit, the control unit including a controller/processor configured to control the drive unit;
    a cartridge, sealingly couplable to the coupling portion of the grippable housing, and containing an injectable fluid;
    the injector unit including a movable plunger driven by the drive unit and extendable in a distal direction beyond the distal end of the grippable housing and into the cartridge to cause extrusion of the injectable fluid from the cartridge when the cartridge is sealingly coupled to the coupling portion;
    an input device, on the portable control unit, configured to receive user input to program the controller/processor to cause extrusion of the fluid from the cartridge at a desired injection rate; and
    a wrist strap removably connectable to the control unit for enabling the control unit to be coupled to a user's wrist during the user's operation of the injector unit.

13. The system of claim 12 wherein the control unit is removably connectable to the wrist strap by magnetic elements.

14. The system of claim 12 wherein the injector unit includes substantially opposing triggers configured to enable ejection of the cartridge from the coupling portion.

15. The system of claim 14 wherein the injector unit housing includes an enlarged distal end defined by substantially opposing, laterally extending flanges and each flange includes one of the substantially opposing triggers.

16. The system of claim 12 wherein the control unit when mounted to a user's wrist, allows the user to view within the same field of vision the control unit and operation of the injector unit.

* * * * *